United States Patent
Araki et al.

(10) Patent No.: US 6,954,264 B2
(45) Date of Patent: Oct. 11, 2005

(54) OPTICAL PULSE TESTING DEVICE

(75) Inventors: Tetsuya Araki, Kumamoto (JP); Makoto Kuratsu, Kumamoto (JP); Katsumi Hirata, Yokohama (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 10/873,793

(22) Filed: Jun. 22, 2004

(65) Prior Publication Data

US 2004/0223136 A1 Nov. 11, 2004

Related U.S. Application Data

(62) Division of application No. 10/376,073, filed on Feb. 27, 2003, now Pat. No. 6,771,361.

(30) Foreign Application Priority Data

Feb. 28, 2002 (JP) ...................................... P.2002-053982

(51) Int. Cl.[7] .............................................. G01N 21/00
(52) U.S. Cl. ..................................................... 356/73.1
(58) Field of Search ....................... 356/73.1; 398/9–38, 398/154–161

(56) References Cited

U.S. PATENT DOCUMENTS 6,614,512 B1 * 9/2003 Sakamoto et al. ......... 356/73.1

2002/0141029 A1 10/2002 Carlson et al.

FOREIGN PATENT DOCUMENTS

| GB | 2126820 A | 3/1984 |
| GB | 2163315 A | 2/1986 |
| GB | 2166020 A | 4/1986 |
| GB | 2202046 A | 9/1988 |

* cited by examiner

*Primary Examiner*—Tu T. Nguyen
(74) *Attorney, Agent, or Firm*—Sughrue Mion, PLLC

(57) ABSTRACT

In order to improve a measuring precision in case of measuring properties of the optical fiber to be measured, in accordance with returned lights which have wavelengths different from each other, detection is carried out with respect to the returned lights of the wavelengths different from each other, at a timing based on difference of propagation rates between the returned lights in the optical fiber to be measured, and error between the returning points is compensated with respect to each returned light, in the optical pulse testing device for inputting the optical pulse to the optical fiber to be measured, to detect returned lights which have wavelengths different from each other and which are returned back from passing points in the optical fiber to be measured, respectively, in order to measure the properties of the optical fiber to be measured, in accordance with detection results of the returned lights.

5 Claims, 4 Drawing Sheets

OPTICAL PULSE TESTING DEVICE

CROSS-REFERENCE TO RELATED APPLICATION(S)

This application is a divisional of U.S. Ser. No. 10/376,073, filed on Feb. 27, 2003 now U.S. Pat. No. 6,771,361.

BACKGROUND OF THE INVENTION

1. Field of the Invention

The present invention relates to an optical pulse testing device for use in measuring various properties of an optical fiber to be measured, on the basis of a returned light of an optical pulse that is obtained from the optical fiber to be measured.

2. Description of the Related Art

As well known in the art, an optical pulse testing device is a device for detecting a back scattered light and a reflected light at each point where an optical pulse passes through in an optical fiber to be measured, to measure various properties of the optical fiber to be measured. In one of the optical pulse testing devices, it is known to detect returned lights whose wavelengths are different from one another, in order to measure a particular property. Inasmuch as propagation rate is dependent on the wavelength of each light in the optical fiber to be measured, returned lights whose wavelengths are different from one another are returned back from points (return points) which are different from one another, when the returned lights are detected at a time. As a result, it is impossible to exactly detect the properties of the optical fiber to be measured, inasmuch as error occurs in each of the return points in case of detecting the returned lights whose wavelengths are different from one another, at a same time.

SUMMARY OF THE INVENTION

Taking the above-mentioned problem into consideration, it is an object of the present invention to provide an optical pulse testing device capable of improving a measuring precision in case of measuring properties of an optical fiber to be measured, in accordance with returned lights which have wavelengths different from one another.

In order to accomplish the above-mentioned object, an optical pulse testing device is for inputting an optical pulse to an optical fiber to be measured, to detect returned lights which have wavelengths different from one another and which are returned back from passing points in the optical fiber to be measured, respectively. The optical pulse testing device measures properties of the optical fiber to be measured, in accordance with detection results of the returned lights, wherein the optical pulse testing device detects each of the returned lights at a timing based on a difference among propagation rates in the optical fiber to be measured, to compensate an error of a return point in each returned light.

The optical testing device may adjust a timing relationship among sampling pulses which are established in the returned lights, respectively, on the basis of the difference among the propagation rates of the returned lights, to compensate the error of the return point in each return light.

The optical pulse testing device may periodically carry out a phase-shift of other sampling pulses with respect to one sampling pulse to adjust the timing relationship among the sampling pulses.

The optical pulse testing device may periodically carry out a phase shift of the timing relationship among the sampling pulses on the basis of a count value of reference clock after inputting the optical pulse into the optical fiber to be measured.

The optical pulse testing device may periodically delay other sampling pulses with respect to one sampling pulse to carry out a phase shifting.

According to the present invention, an optical pulse testing device is for inputting an optical pulse which has one selected from a plurality of wavelengths to an optical fiber to be measured, to detect returned lights which are returned back from passing points in the optical fiber to be measured, respectively. The optical pulse testing device measures properties of the optical fiber to be measured, in accordance with detection results of the returned lights, wherein the optical pulse testing device adjusts a detection timing of returned lights corresponding to an optical pulse having another wavelength, with respect to a detection timing of returned lights corresponding to an optical pulse having a reference wavelength selected from the plurality of wavelengths, in accordance with a difference among the propagation rates of the wavelengths, to compensate an error of a return point in each returned light.

The optical testing device may adjust a timing relationship among sampling pulses which are established in the returned lights, respectively, on the basis of the difference among the propagation rates of the returned lights, to compensate the error of the return point in each return light.

The optical pulse testing device may periodically carry out a phase shift of other sampling pulses which are established to returned lights corresponding to optical pulses having other wavelengths, with respect to one sampling pulse which is established to the returned lights corresponding to the optical pulse having the reference wavelength, to adjust the timing relationship among the sampling pulses.

The optical pulse testing device may periodically carry out a phase shift of the timing relationship among the sampling pulses on the basis of a count value of reference clock after inputting the optical pulse into the optical fiber to be measured.

The optical pulse testing device may periodically delay other sampling pulses with respect to one sampling pulse to carry out a phase shifting.

PREFERRED EMBODIMENTS OF THE INVENTION

With reference to drawings, description will be made as regards embodiments of an optical pulse testing device according to the present invention.

First Embodiment

Figure 1:
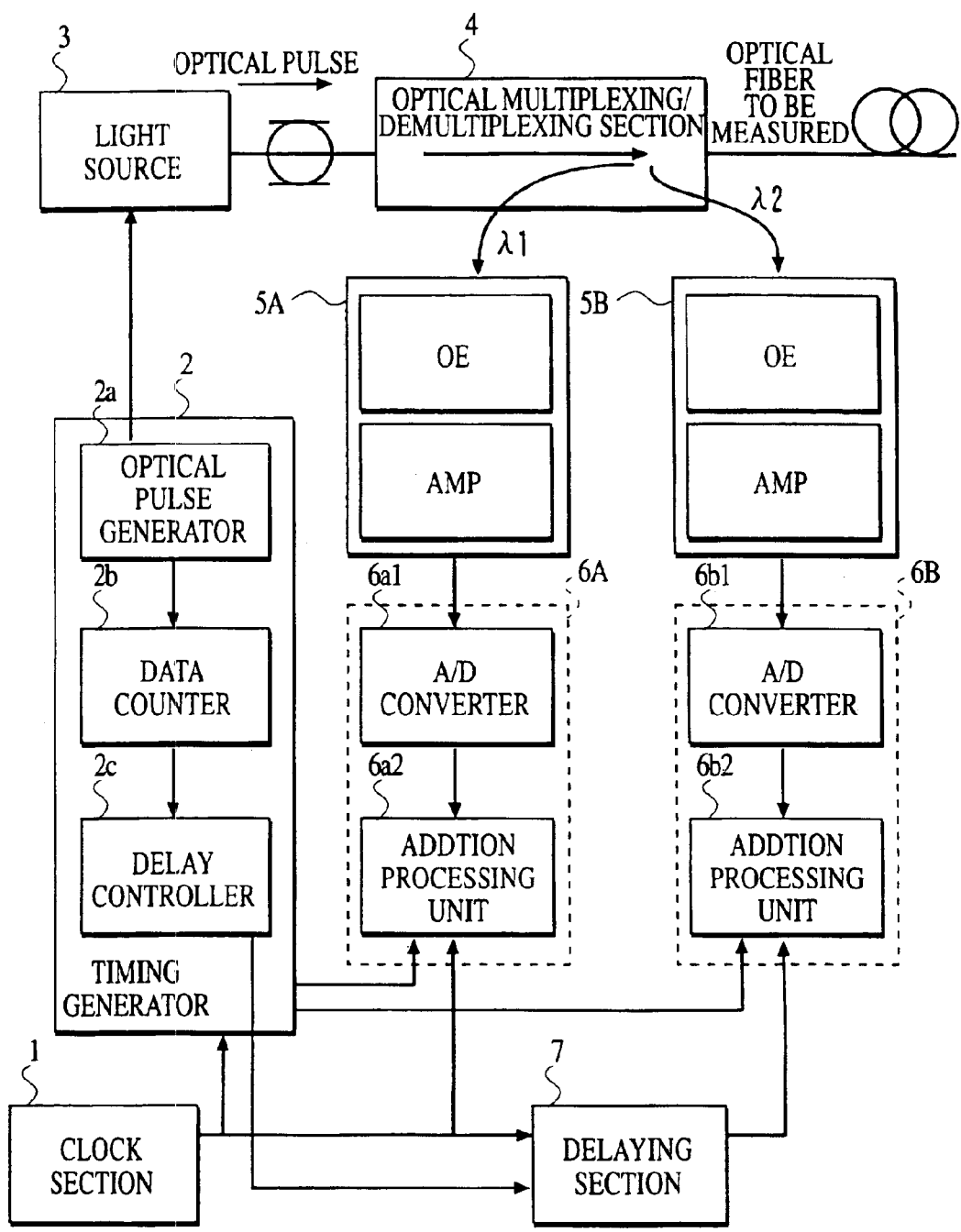
FIG. 1 is a block diagram for illustrating a main configuration according to a first embodiment of the present invention.

At first, description will be made about a first embodiment. FIG. 1 is a block diagram for illustrating a main configuration of an optical pulse testing device according to the first embodiment. In FIG. 1, a reference numeral 1 represents a clock section. A reference numeral 2 represents a timing generator. A reference numeral 3 represents a light source. A reference numeral 4 represents optical multiplexing/demultiplexing section. Each of reference numerals 5A and 5B represents a returned light receiving section. Each of reference numerals 6A and 6B represents a returned light detecting section. A reference numeral 7 represents a delaying section. Incidentally, the optical pulse testing device according to the first embodiment measures a particular property of an optical fiber to be measured, using returned lights having wavelengths λ1 and λ2, respectively, that are obtained from the optical fiber to be measured, when inputting an optical pulse into the optical fiber to be measured.

The clock section 1 generates a reference clock which is used on carrying out various processes described hereinafter, to supply the reference clock to the timing generator 2, the returned light detecting section 6A, and the delaying section 7. On the basis of the reference clock, the timing generator 2 produces various pulses which is for use in controlling the light source 3, returned light detecting sections 6A and 6B, and the delaying section 7, respectively. The timing generator 2 comprises an optical pulse generator 2a, a data counter 2b, and a delay controller 2c.

The optical pulse generator 2a generates an optical pulse timing signal at a predetermined time interval in accordance with the reference clock to output the optical pulse timing signal to the light source 1. Using the optical pulse timing signal as a trigger signal, the data counter 2b starts a count of the reference clock to output the count value to the delay controller 2c. The delay controller 2c produces a delay control signal on the basis of the above-mentioned count value to output the delay control signal to the delaying section 7.

In synchronization with the optical pulse timing signal which is supplied from the optical pulse generator 2a, the light source 3 generates or emits an optical pulse having a single wavelength, to output the optical pulse to the optical multiplexing/demultiplexing section 4.

The optical multiplexing/demultiplexing section 4 is an optical directional coupler having a wavelength branching function, to transmit the optical pulse to the optical fiber to be measured. Furthermore, the optical multiplexing/demultiplexing section 4 selects the returned light having the wavelength λ1 from the various returned lights which are inputted from the optical fiber to be measured, to output the returned light having the wavelength λ1 to the returned light receiving section 5A. In addition, the optical multiplexing/demultiplexing section 4 selects the returned light having the wavelength λ2 from the various returned lights, to output the returned light having the wavelength λ2 to the returned light receiving section 5B. Each of the returned light receiving sections 5A and 5B comprises an optical/electrical converter and an amplifier.

The returned light receiving section 5A converts the returned light having the wavelength λ1 into an electrical signal by the optical/electrical converter to amplify the electrical signal and to output the amplified electrical signal as a first reception signal to the returned light detecting section 6A. In addition, the returned light receiving section 5B converts the returned light having the wavelength λ2 into an electrical signal by the optical/electrical converter to amplify the electrical signal and to output the amplified electrical signal as a second reception signal to the returned light detecting section 6B.

In the example being illustrated, the returned light detecting sections 6A and 6B comprise A/D converters 6a1 and 6b1 and addition processing units 6a2 and 6b2, respectively. In the returned light detecting section 6A, the A/D converter 6a1 samples the first reception signal in accordance with the reference clock which is a first sampling pulse, to convert the first reception signal into discrete and sequential data which are outputted to the addition processing unit 6a2. The addition processing unit 6a2 carries out averaging process with respect to the sampling data which correspond to a plurality of optical pulses, in order to improve an S/N ratio of signal. The addition processing unit 6a2 outputs the result obtained by the averaging process, to a measurement arithmetic section which is not illustrated.

In the returned light detecting section 6B, the A/D converter 6b1 samples the second reception signal in accordance with a delay clock supplied from the delaying section 7 that is a second sampling pulse, to convert the second reception signal into discrete and sequential data which are outputted to the addition processing unit 6b2. The addition processing unit 6b2 carries out averaging process with respect to the sampling data which correspond to a plurality of optical pulses, in order to improve an S/N ratio of signal. The addition processing unit 6b2 outputs the result obtained by the averaging process, to the measurement arithmetic section which is not illustrated.

The delaying section 7 is a characteristic component in the first embodiment. The delaying section 7 gives a delay to the reference clock in accordance with the delay control signal which is inputted from the timing generator 2, to produce the delay clock which is supplied to the returned light detecting section 6B. Incidentally, the operation of the delaying section 7 will be described in detail hereinafter.

Figure 2:
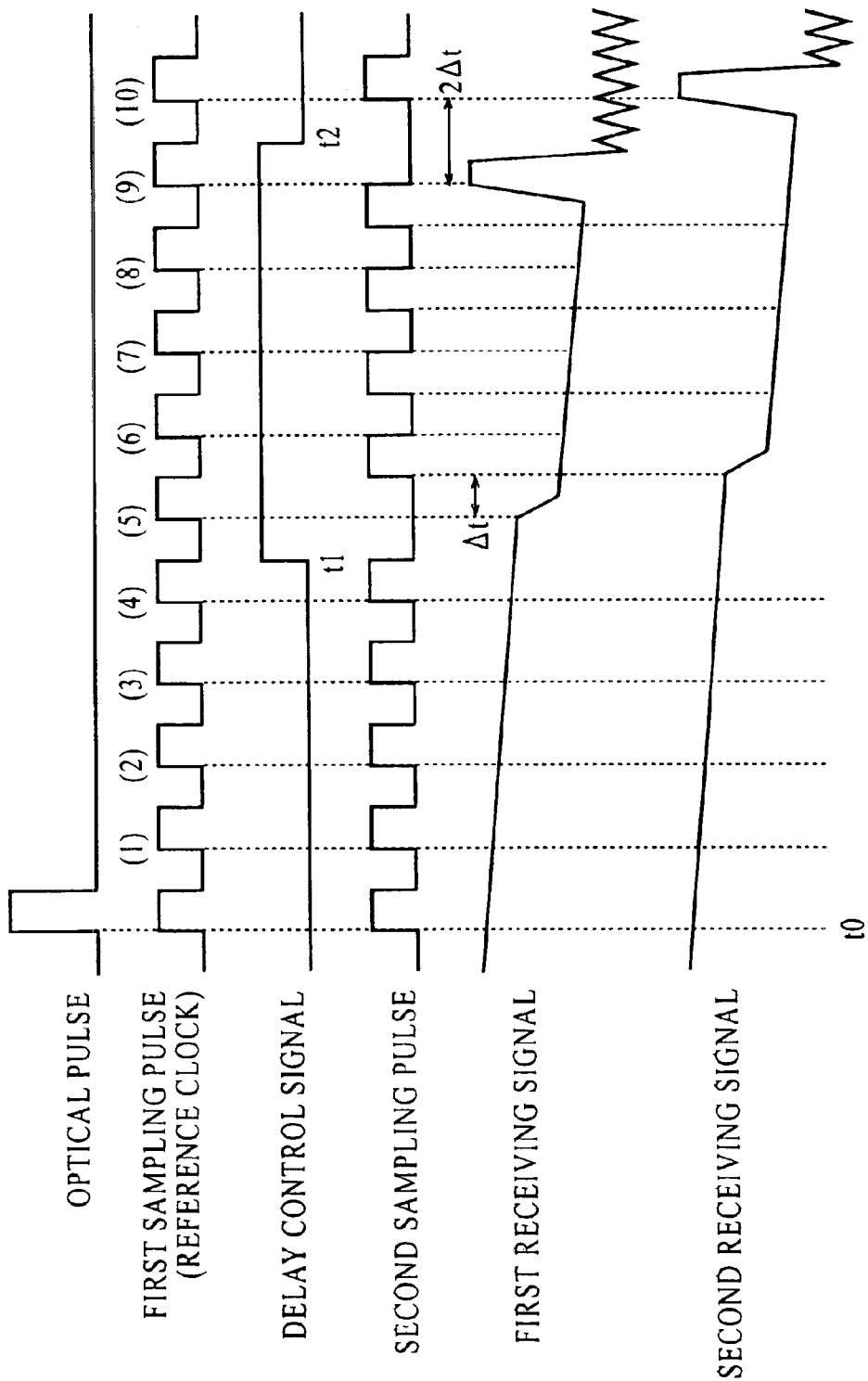
FIG. 2 is a timing chart for describing an operation of the first embodiment of the present invention.

Next, description will be made as regards a detailed operation of the first embodiment with reference to FIG. 2. FIG. 2 is a timing chart for illustrating a timing relationship of the above-mentioned various signals and the first and the second reception signals.

Inasmuch as the first reception signal has a propagation rate different from that of the second reception signal, in the optical fiber to be measured, a time lag $\Delta t$ occurs between the first reception signal and the second reception signal at timings when inputting the returned lights to the returned light receiving sections 5A and 5B, respectively. The time lag $\Delta t$ is variable on the basis of the wavelengths λ1 and λ2 of the returned lights which concern to the first and the second reception signals and on the basis of a wavelength difference between the wavelength λ1 and λ2. In the first embodiment, the second sampling pulse is periodically varied in timing for the first sampling pulse as shown in the drawing, in order to detect the returned lights having the wavelengths λ1 and λ2 that are returned from a same return point, by compensating the time lag $\Delta t$.

In other words, the timing generator 2 makes the optical pulse generator 2a supply the optical pulse timing signal to the light source 3, in order to input the optical pulse synchronized with the optical pulse timing signal, from the light source 3 to the optical fiber to be measured. As a result, the data counter 2b starts the count of the first sampling pulse which is the reference clock. When the count value of the data counter 2b is equal to four, the delay controller 2c transfers the delay control signal from a low level to a high level at a timing t1.

As a result, the sampling timing is varied in the time lag $\Delta t$ with respect to the second reception signal in the A/D converter 6b1 of the returned light detecting section 6B, inasmuch as the delaying section 7 supplies the returned light detecting section 6B with the second sampling pulse which is obtained by giving a delay of $\Delta t$ to the reference clock. In other words, the returned light detecting section 6B detects the returned light of the second reception signal that is returned at the same returning point where the returned light of the first reception signal is returned which is concerned to the A/D converter 6a1 of the returned light detecting section 6A.

Inasmuch as the data counter 2b does not carry out the count of a first pulse in the first sampling pulse (reference clock) that rise at a emission timing t0 of the optical pulse, the delay controller 2c transfers the delay control signal at a timing when the above-mentioned count value is equal to four. In other words, the above-mentioned timing is a timing when five clocks lapse in the reference clock from the emission timing t0 of the optical pulse.

The data counter 2b continues the count of the reference clock even though the above-mentioned timing t1 lapses. When the count value is equal to nine (=4+5) in the data counter 2b, namely, after the timing t1 lapses, the delay controller 2c changes the delay control signal from the high level to the low level at the timing t2 when five clocks lapse in the reference clock as described above. As a result, the delaying section 7 resets a state in which the delay of the time lag $\Delta t$ is given to the reference clock and changes the second sampling pulse to a state in which the second sampling pulse has a timing same to that of the first sampling pulse. Accordingly, the second sampling pulse has double time lag $\Delta t$ that is $2\Delta t$ for the first sampling pulse.

Therefore, the sampling timing of the first reception signal is varied in $2\Delta t$ for the sampling timing of the second reception signal, in the A/D converter 6b1 of the returned light detecting section 6B. After that, the level of the delay control signal is transferred every time there is an increase of five clocks in the count value of the data counter 2b. The timing of the second reception signal is compensated every five clocks so that the return point concerned to the second reception signal is coincident to the return point concerned to the first reception point.

As described above, it is possible to correctly measure the property of the optical fiber to be measured, on the basis of the returned lights which have the wavelengths $\lambda 1$ and $\lambda 2$, respectively, inasmuch as the time lag $\Delta t$ between reception times is compensated at each time interval which corresponds to five pulses of the reference clock with respect to the returned lights having wavelengths $\lambda 1$ and $\lambda 2$ which are returned from the same return point, according to the first embodiment of the present invention.

Incidentally, it is applicable to measure the property of the optical fiber to be measured, using three and more wavelengths, without being limited to two wavelengths $\lambda 1$ and $\lambda 2$, although the optical pulse testing device of the first embodiment measures the property of the optical fiber to be measured, on the basis of the returned lights which have the wavelengths $\lambda 1$ and $\lambda 2$, respectively.

Second Embodiment

Next, description will proceed to an optical pulse testing device according to a second embodiment of the present invention. Incidentally, the optical pulse testing device of the second embodiment emits a selected one of a plurality of optical pulses which have wavelengths different from one another. The optical pulse testing device of the second embodiment receives the returned light of single wavelength that is based on the selected optical pulse having a particular wavelength, to measure the property of the optical fiber to be measured. In following description, the parts similar to the first embodiment are designated by like reference numerals in the second embodiment and description will be omitted.

Figure 3:
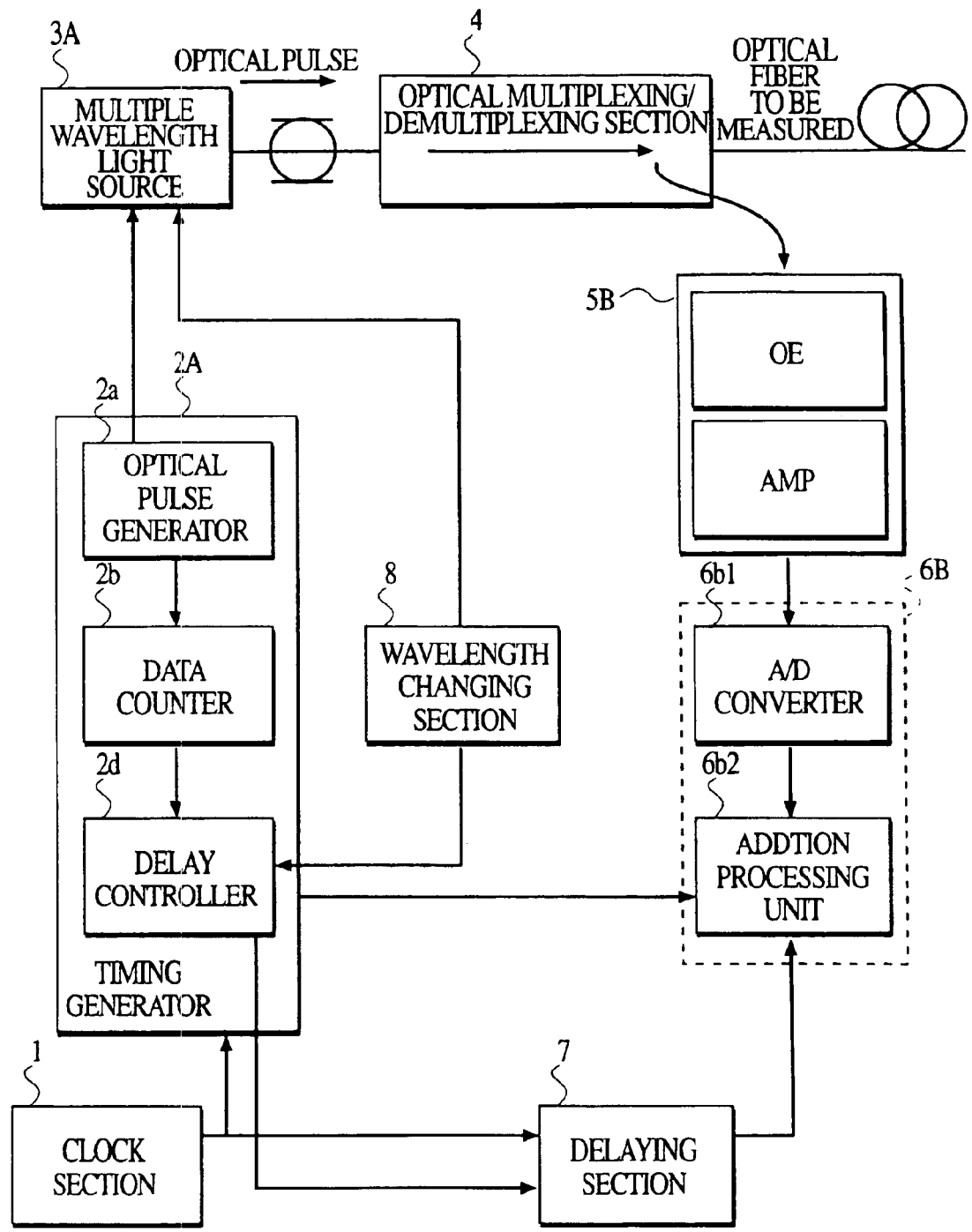
FIG. 3 is a block diagram for illustrating a main configuration according to a second embodiment of the present invention.

FIG. 3 is a block diagram for illustrating a main configuration of the optical pulse testing device according to the second embodiment of the present invention. A timing generator 2A comprises a delay controller 2d which is different in structure from the delay controller 2c of the timing generator 2 according to the first embodiment, in the second embodiment of the present invention. In other words, the delay controller 2d of the optical pulse testing device controls the delaying section 7 on the basis of a wavelength selection signal inputted from a wavelength changing section 8, in addition to the count value supplied from the data counter 2b. A multiple wavelength light source 3A emits a selected one of optical pulses that has a particular wavelength selected from a plurality of wavelengths (for example, wavelengths $\lambda 1$ and $\lambda 2$), on the basis of the wavelength selection signal. The wavelength changing section 8 is for supplying the above-mentioned wavelength selection signal to the delay controller 2d and the multiple wavelength light source 3A in accordance with a manual operation.

In the above-mentioned optical pulse testing device, the multiple wavelength light source 3A emits the optical pulse of wavelength $\lambda 1$ or $\lambda 2$ which is selected in accordance with the wavelength selection signal, in order to input the optical pulse into the optical fiber to be measured. The propagation rate of the returned light corresponding to the optical pulse of the wavelength $\lambda 1$ is different from the propagation rate of the returned light corresponding to the optical pulse of the wavelength $\lambda 2$, in the optical fiber to be measured. In case of detecting the returned lights having the wavelengths $\lambda 1$ and $\lambda 2$, respectively, at a same sampling timing, the sampled values are obtained by sampling the returned lights which are returned from the return points different from each other. In this case, it is necessary to compensate the sampling timing of the returned light having the wavelength $\lambda 2$, in accordance with the sampling timing of the returned light having the wavelength $\lambda 1$, inasmuch as a lag occurs between return point of the returned light having the wavelength $\lambda 1$ and the return point of the returned light having the wavelength $\lambda 2$.

Figure 4:
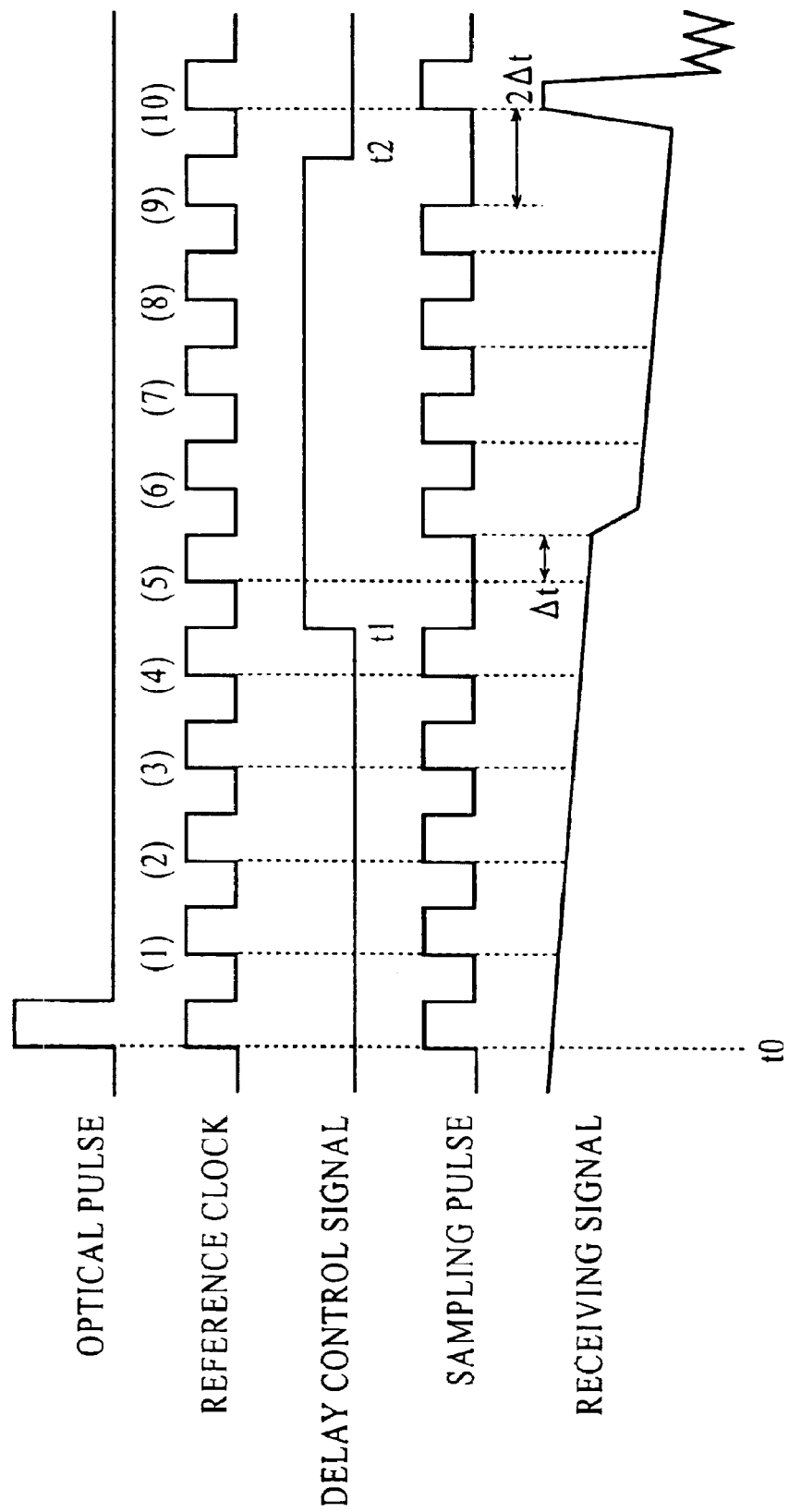
FIG. 4 is a timing chart for describing an operation of the second embodiment of the present invention.

Under the circumstances, the optical pulse testing device according to the second embodiment changes the sampling timing corresponding to the returned light of the wavelength $\lambda 2$ at a time duration corresponding to five pluses of the reference clock on a one-by-one interval $\Delta t$, as shown in FIG. 4 in a manner similar to the first embodiment. More particularly, the delay controller 2d produces the delay control signal on the basis of the wavelength selection signal and the count value of the data counter 2b. The delaying operation of the delaying section 7 is controlled in accordance with the delay control signal. The sampling pulses for the returned light of the wavelength $\lambda 2$ are delayed on one-by-one interval $\Delta t$. As a result, the sampling timing for the returned light of the wavelength $\lambda 2$ is modified at each time duration corresponding to five pulses, in accordance with the sampling timing for the returned light of the wavelength $\lambda 1$.

Incidentally, the interval $\Delta t$ which is a compensating minimum unit becomes a different interval in case where one of wavelength $\lambda 3$, $\lambda 4$, . . . is selected instead of the wavelength $\lambda 2$. More specifically, the delay controller 2d supplies the delaying section 7 with a delaying amount based on the wavelength of the optical pulse that is selected by the wavelength changing section 8. As a result, the delaying section 7 gives a delay to the sampling pulses in accordance with the delaying amount based on the selected one of the wavelengths $\lambda 2$, $\lambda 3$, $\lambda 4$, . . . .

As described above, it is possible to improve the measuring precision in case of measuring properties of the optical fiber to be measured, in accordance with returned lights which have wavelengths different from one another, because of detecting the returned lights of the wavelengths different from one another, at the timing based on the difference of the propagation rates between the returned lights in the optical fiber to be measured, and the error is compensated with respect to the returning points, in the optical pulse testing device for inputting the optical pulse to the optical fiber to be measured, to detect returned lights which have wavelengths different from one another and which are returned back from passing points in the optical fiber to be measured, respectively, in order to measure the properties of the optical fiber to be measured, in accordance with detection results of the returned lights, according to the present invention.

What is claimed is:

1. An optical pulse testing device comprising:
   an optical multiplexer/demultiplexer to provide an optical pulse having a first wavelength and an optical pulse having a second wavelength, selected from a plurality of wavelengths, to an optical fiber to be measured,
   a detection section to detect returned optical signals which are returned back from points in the optical fiber,
   a processing section to measure properties of the optical fiber in accordance with detection results of the returned optical signals, and
   a delay section adapted to adjust a detection timing of returned optical signals based on a difference among propagation rates between the optical pulse having a first wavelength and the optical pulse having a second wavelength, to compensate for an error of a return point in each returned optical signal.

2. An optical pulse testing device as claimed in claim 1, wherein the delay section is adapted to adjust a timing relationship among sampling pulses for the returned optical signals, respectively, on the basis of the difference among the propagation rates to compensate for the error of the return point in each returned optical signal.

3. An optical pulse testing device as claimed in claim 2, wherein the the delay section is adapted to periodically carry out a phase-shift of other sampling pulses which are established to returned optical signals corresponding to optical pulses having a second wavelength, with respect to one sampling pulse which is established to the returned optical signals corresponding to the optical pulse having a first wavelength, to adjust the timing relationship among the sampling pulses.

4. An optical pulse testing device as claimed in claim 3, comprising a reference clock, wherein the delay section is adapted to periodically carry out a phase shift of the timing relationship among the sampling pulses on the basis of a count value of the reference clock after inputting the optical pulse into the optical fiber to be measured.

5. An optical pulse testing device as claimed in claim 3, wherein the delay section is adapted to periodically delay the other sampling pulses with respect to one sampling pulse to carry out a phase shifting.

* * * * *